US008822546B2

(12) United States Patent
Benz et al.

(10) Patent No.: US 8,822,546 B2
(45) Date of Patent: Sep. 2, 2014

(54) FLOWABLE PHARMACEUTICAL DEPOT

(75) Inventors: Michael Eric Benz, Ramsey, MN (US); Christopher M. Hobot, Tonka Bay, MN (US); Phillip Edward McDonald, Plymouth, MN (US); Lian Leon Luo, Shoreview, MN (US); John Kramer, Mt. Pleasant, MI (US)

(73) Assignee: Medtronic, Inc., Minneapolis, MN (US)

( * ) Notice: Subject to any disclaimer, the term of this patent is extended or adjusted under 35 U.S.C. 154(b) by 401 days.

(21) Appl. No.: 12/325,514

(22) Filed: Dec. 1, 2008

(65) Prior Publication Data

US 2010/0137369 A1 Jun. 3, 2010

(51) Int. Cl.
*A61K 31/045* (2006.01)
*A61K 47/34* (2006.01)
*A61K 31/4168* (2006.01)
*A61K 9/00* (2006.01)
*A61K 31/445* (2006.01)

(52) U.S. Cl.
CPC ............... *A61K 9/0024* (2013.01); *A61K 47/34* (2013.01); *A61K 31/4168* (2013.01); *A61K 31/445* (2013.01)
USPC ............................ 514/724; 514/772.1; 523/1

(58) Field of Classification Search
USPC ..................................... 514/724, 772.1; 523/1
See application file for complete search history.

(56) References Cited

U.S. PATENT DOCUMENTS

| 3,190,802 | A | 6/1965 | Zeile et al. |
|---|---|---|---|
| 3,020,660 | A | 8/1965 | Zeile et al. |
| 4,765,974 | A | 8/1988 | Tokuda et al. |
| 4,938,763 | A | 7/1990 | Dunn et al. |
| 5,175,052 | A | 12/1992 | Tokuda et al. |
| 5,447,947 | A | 9/1995 | Campbell |
| 5,484,607 | A | 1/1996 | Horacek |
| 5,635,204 | A | 6/1997 | Gevirtz et al. |
| 5,801,188 | A | 9/1998 | Hassenbusch, III et al. |
| 5,869,100 | A | 2/1999 | Horacek |
| 5,889,110 | A | 3/1999 | Hutchinson |
| 5,942,503 | A | 8/1999 | Jung et al. |
| 5,942,530 | A | 8/1999 | Panetta et al. |
| 5,945,416 | A | 8/1999 | Shannon et al. |
| 5,980,927 | A | 11/1999 | Nelson et al. |
| 6,030,642 | A | 2/2000 | Horacek |
| 6,147,102 | A | 11/2000 | Borgman |
| 6,413,536 | B1 | 7/2002 | Gibson et al. |
| 6,417,184 | B1 | 7/2002 | Ockert |
| 6,534,048 | B1 | 3/2003 | Borgman |
| 6,565,874 | B1 | 5/2003 | Dunn et al. |
| 6,589,548 | B1 | 7/2003 | Oh et al. |
| 6,992,110 | B2 | 1/2006 | Kranzler et al. |
| 7,345,065 | B2 | 3/2008 | Gil et al. |
| 7,507,398 | B2 | 3/2009 | Rabinowitz et al. |
| 7,524,812 | B2 | 4/2009 | Ellis et al. |
| 2002/0058656 | A1 | 5/2002 | Ockert |
| 2002/0094998 | A1 | 7/2002 | Burke et al. |
| 2003/0022926 | A1 | 1/2003 | Lavand'Homme |
| 2003/0224033 | A1 | 12/2003 | Li et al. |
| 2004/0028726 | A1 | 2/2004 | Fischer et al. |
| 2004/0101582 | A1 | 5/2004 | Wolicki |
| 2004/0208917 | A1 | 10/2004 | Fischer et al. |
| 2004/0265364 | A1 | 12/2004 | Ozturk et al. |
| 2005/0058696 | A1 | 3/2005 | Donello et al. |
| 2005/0059744 | A1 | 3/2005 | Donello et al. |
| 2005/0095277 | A1 | 5/2005 | Ozturk et al. |
| 2006/0009806 | A1 | 1/2006 | Heruth et al. |
| 2006/0253100 | A1 | 11/2006 | Burright et al. |
| 2007/0141160 | A1 | 6/2007 | Brown et al. |
| 2007/0207213 | A1 | 9/2007 | Chu et al. |
| 2008/0152709 | A1 | 6/2008 | Bortz |
| 2008/0171075 | A1 | 7/2008 | Ozturk et al. |
| 2009/0264472 | A1* | 10/2009 | Wohabrebbi et al. ......... 514/330 |
| 2009/0264491 | A1* | 10/2009 | McKay et al. ................ 514/401 |

FOREIGN PATENT DOCUMENTS

| EP | 0251631 A1 | 1/1988 |
|---|---|---|
| EP | 1917971 A1 | 5/2008 |
| WO | 2006011915 A1 | 2/2006 |
| WO | 2006022611 A2 | 3/2006 |
| WO | 2006078320 A2 | 7/2006 |
| WO | 2006101540 A1 | 9/2006 |
| WO | 2008079868 A1 | 7/2008 |
| WO | 2009100441 A2 | 8/2009 |
| WO | WO 2009129437 | * 10/2009 |
| WO | WO 2009129509 | * 10/2009 |

OTHER PUBLICATIONS

Nederberg, et al., "Organocatalytic Chain Scission of Poly(lactides): a General Route to Controlled Molecular Weight, Functionality and Macromolecular Architecture", Chem. Communication,:2066-2067, 2001.
Sharifpoor, et al., "In-vitro Release of a Water-Soluble Agent from Low Viscosity Biodegrabable, Injectable Oligomers", European Journal of Pharmaceutics and Biopharmaceutics, 65:336-345, 2007.
International Search Report and Written Opinion for US Application PCT/US2009/066107 mailed on Dec. 14, 2010.
Jarr,, E.M., et al., Sustained Release of Lidocaine from an Injectable Implant System for Treatment of Post-Operative Pain, Proceedings of the International Symposium on Controlled Release Bioactive Materials, Controlled Release Society, Inc., US; KR, vol. 26, Jul. 1, 1999, p. 631/632, XP002133945, ISSN: 1022-0178, pp. 631-632.
Kurokawa et al., "Surface properties and enzymatic degradation of end-capped poly(l-lactide)", Polymer Degradation and Stability, Barking, GB, vol. 91, No. 6, Jun. 1, 2006, pp. 1300-1310, XP025095776, ISSN: 0141-3910, DOI: DOI:10.1016/J. Polymdegradstab.2005.08.015, [retrieved on Jun. 1, 2006], abstract.
Zou, et al. "Synthesis and characterization of end-capped biodegradable oligo/poly(trimethylene carbonate)s", Journal of Biomaterials Science, Polymer Edition, VSP, Utrecht, NL, vol. 17, No. 10, Jan. 1, 2006, pp. 1093-1106, XP008130137, ISSN: 0920-5063, DOI: DOI:10.1163/156856206778530687, abstract.

* cited by examiner

*Primary Examiner* — Renee Claytor
*Assistant Examiner* — Shobha Kantamneni
(74) *Attorney, Agent, or Firm* — Sorell Lenna & Schmidt LLP

(57) ABSTRACT

Flowable pharmaceutical depots are described. The flowable pharmaceutical depot includes a polyester, such as a polylactic acid or a poly(trimethylene carbonate) endcapped with a primary alcohol and a pain relieving therapeutic agent, such as a post operative pain relieving therapeutic agent. Method of making and using the same are also described.

4 Claims, 2 Drawing Sheets

US 8,822,546 B2

FLOWABLE PHARMACEUTICAL DEPOT

BACKGROUND

This disclosure relates to flowable pharmaceutical depots that contribute to the local treatment of pain.

Pain can be divided into two types: nociceptive pain and neuropathic pain. Acute nociceptive pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends.

Post-operative pain is a result of a surgical procedure. Traditional surgical procedures for pathologies located deep within the body can cause significant trauma to the intervening tissues. These open procedures can often require a long incision, extensive muscle stripping, prolonged retraction of tissues, denervation and devascularization of tissue. Many of these surgeries require a recovery room time of several hours and several weeks of post-operative recovery time due to the use of general anesthesia and the destruction of tissue during the surgical procedure. In some cases, these invasive procedures lead to permanent scarring and chronic pain that can be more severe than the pain leading to the surgical intervention.

BRIEF SUMMARY

The present disclosure relates to flowable pharmaceutical depots. In particular, the present disclosure relates to flowable pharmaceutical depots that include biodegradable polyesters and a post-operative pain relieving therapeutic agent.

In one particular embodiment, a flowable pharmaceutical depot includes a polylactic acid endcapped with a primary alcohol or a poly(trimethylene carbonate) and a post-operative pain relieving therapeutic agent. Method of making and using the same are also described.

In another embodiments, a pharmaceutical depot includes a biogdegradable polyester endcapped with a primary alcohol and a pain relieving therapeutic agent.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
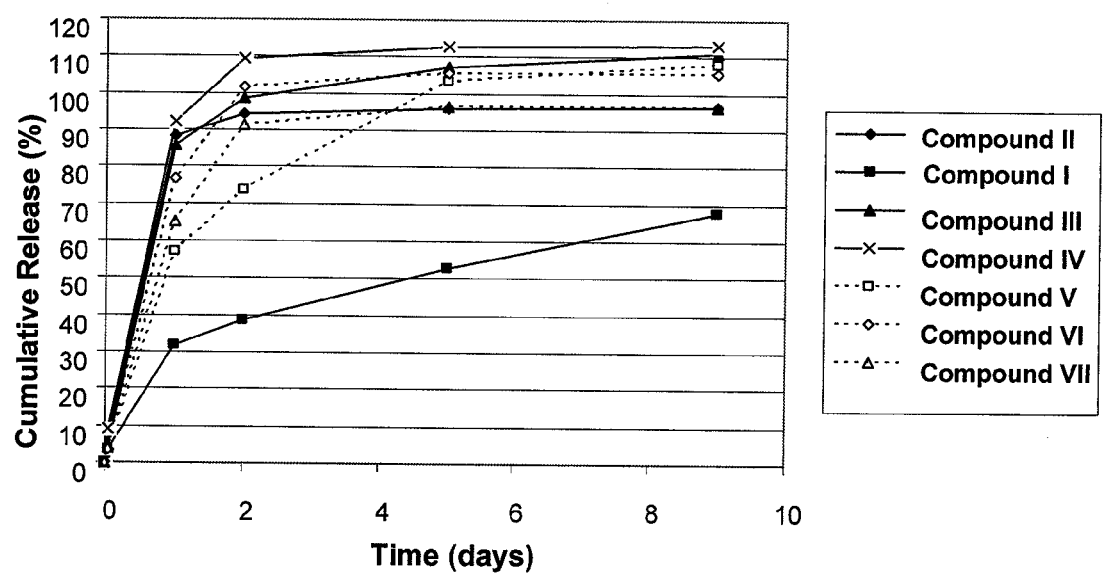
FIG. 1 is a graph of cumulative release of bupivacaine loaded PLA pharmaceutical depots.

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (e.g. 1 to 5 includes 1, 1.5, 2, 2.75, 3, 3.80, 4, and 5) and any range within that range.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

The present disclosure relates to flowable pharmaceutical depots. In particular, the present disclosure relates to flowable pharmaceutical depots that include biodegradable polyesters and a pain relieving therapeutic agent such as, for example, a post-operative pain relieving therapeutic agent. The biodegradable polyesters include polylactic acid (i.e., PLA) endcapped with a primary alcohol such as, for example, dodecanol, and/or poly(trimethylene carbonate) (i.e., PTMC) endcapped with a primary alcohol such as, for example, dodecanol. The flowable pharmaceutical depots have a viscosity low enough for injection and have been shown to provide long duration therapeutic agent release in vivo. While the present disclosure is not so limited, an appreciation of various aspects of the disclosure will be gained through a discussion of the examples provided below.

The flowable pharmaceutical depots include a biodegradable polyester and a post-operative pain relieving therapeutic agent. The pharmaceutical depot is flowable, for example, the pharmaceutical depot can be administered via a syringe and the like. In many embodiments the pharmaceutical depot provides a long duration therapeutic agent release in vivo, for example, for at least 3 days, or for at least 5 days, or for at least 10 days or for at least 20 days, as desired. In many embodiments the flowable pharmaceutical depot has a viscosity in a range from 0.001 to 1000 Pa·s, or in a range from 0.1 to 500 Pa·s, or in a range from 1 to 200 Pa·s, or in a range from 1 to 100 Pa·s. The flowable pharmaceutical depots can be injected in to a surgical wound to provide extended release of the post-operative pain relieving therapeutic agent. The flowable pharmaceutical depot provides effective space filling of the surgical would and can evenly distribute the post-operative pain relieving therapeutic agent to all areas of the surgical wound space. In many embodiments, the flowable pharmaceutical depot does not cure or cross-link once administered in vivo. In many embodiments, the flowable pharmaceutical depot includes a flowable biodegradable polyester and pain relieving therapeutic agent. In many of these embodiments, the flowable pharmaceutical depot is substantially formed of only includes a flowable biodegradable polyester and pain relieving therapeutic agent.

Viscosity was measured at room temperature (25 degrees centigrade) from the dependence of shear viscosity on shear rate determined from an Ares (Rheometric Scientific, Piscataway, N.J.), using parallel 25 millimeter plates typically with a frequency sweep from 100 to 0.01 (1/s). Zero shear viscosity of a sample was obtained when a constant viscosity over a range of at least one decade of shear rate was achieved.

The biodegradable polyester can be any useful polyester that degrades over time in vivo. Illustrative biodegradable polyesters include a polylactic acid (i.e., PLA) endcapped with a primary alcohol such as, for example, dodecanol, and/or a poly(trimethylene carbonate) (i.e., PTMC) endcapped with a primary alcohol such as, for example, dodecanol. In some applications the degree of tissue wetting is a desired physical property of the selected biodegradable polyester. Biodegradable polyesters that wet tissue and remained adherent and spread out after wound closure, for example, are desirable.

Biodegradable polyesters include, for example, polylactides, polyglycolides, polycaprolactone, copolymers thereof, terpolymers thereof, and any combinations thereof. In many embodiments the biodegradable polyester is a polylactide, a polyglycolide, a copolymer thereof, or a combination thereof.

In many embodiments, the polylactic acid can be depolymerized and endcapped with a suitable alcohol to form a polymer of suitable average molecular weight and viscosity. In other embodiments, the polylactic acid can be polymerized to form a polymer of suitable average molecular weight and viscosity. As shown in the EXAMPLE section below, the release profile of the post-operative pain relieving therapeutic agent varies according to the particular primary alcohol used to endcap the polylactic acid. The polylactic acid can be endcapped with a primary alcohol has an average molecular weight in a range from 10 to 10000 g/mol, or in a range from 100 to 3000 g/mol, or in a range from 500 to 3000 g/mol, or in a range from 500 to 2000 g/mol. In some embodiments the biodegradable polyester is a blend of two or more endcapped polylactic acids where each endcapped polylactic acid has a different average molecular weight and may be endcapped with different alcohols. The viscosity of the polylactic acid endcapped with a suitable primary alcohol is substantially the same as the viscosity of the flowable pharmaceutical depot, as described above.

One useful primary alcohol is dodecanol which provides a dodecyl end group on the polylactic acid. This compound is identified as Compound I in FIG. 1. As illustrated in FIG. 1, the release profile of the post-operative pain relieving therapeutic agent utilizing Compound I is surprisingly extended as compared to other compounds endcapped with structurally similar alcohols. Another useful primary alcohol is methanol which provides a methyl end group on the polylactic acid. This compound is identified as Compound V in FIG. 1. As illustrated in FIG. 1, the release profile of the post-operative pain relieving therapeutic agent utilizing Compound V is surprisingly extended as compared to other compounds endcapped with structurally similar alcohols.

In another embodiment, poly(trimethylene carbonate) can be polymerized and endcapped with a suitable primary alcohol. In many embodiments the (trimethylene carbonate) can be polymerized and endcapped with dodecanol. As shown in the EXAMPLE section below, the release profile of the post-operative pain relieving therapeutic agent varies according to the particular molecular weigh and/or viscosity of the poly(trimethylene carbonate). The poly(trimethylene carbonate) endcapped with a primary alcohol has an average molecular weight in a range from 100 to 10000 g/mol, or in a range from 500 to 3000 g/mol, or in a range from 500 to 2000 g/mol. In some embodiments the biodegradable polymer is a blend of two or more endcapped poly(trimethylene carbonate)s where each endcapped poly(trimethylene carbonate) has a different average molecular weight and may be endcapped with different alcohols. The viscosity of the poly(trimethylene carbonate) endcapped with a suitable primary alcohol is substantially the same as the viscosity of the flowable pharmaceutical depot.

Figure 2:
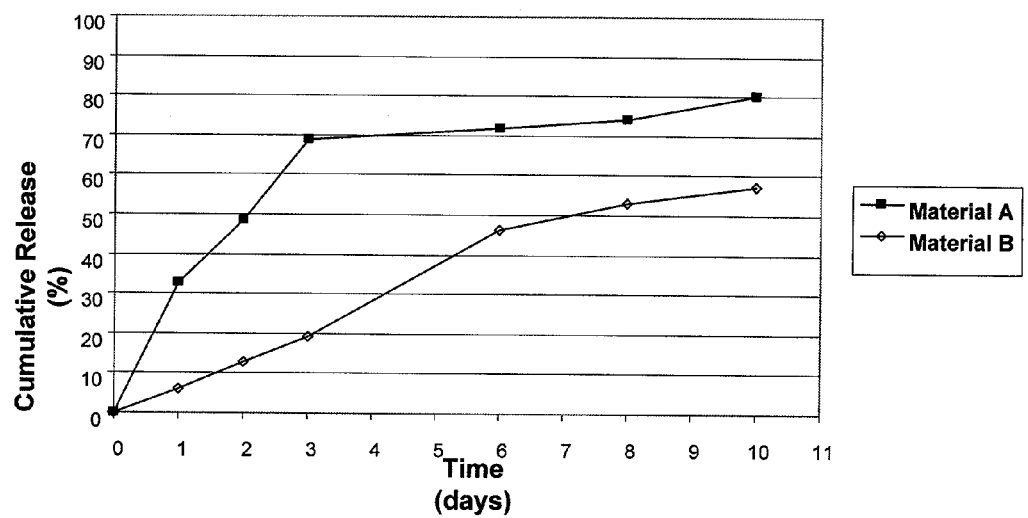
FIG. 2 is a graph of cumulative release of clonidine loaded PTMC pharmaceutical depots.
Figure 3:
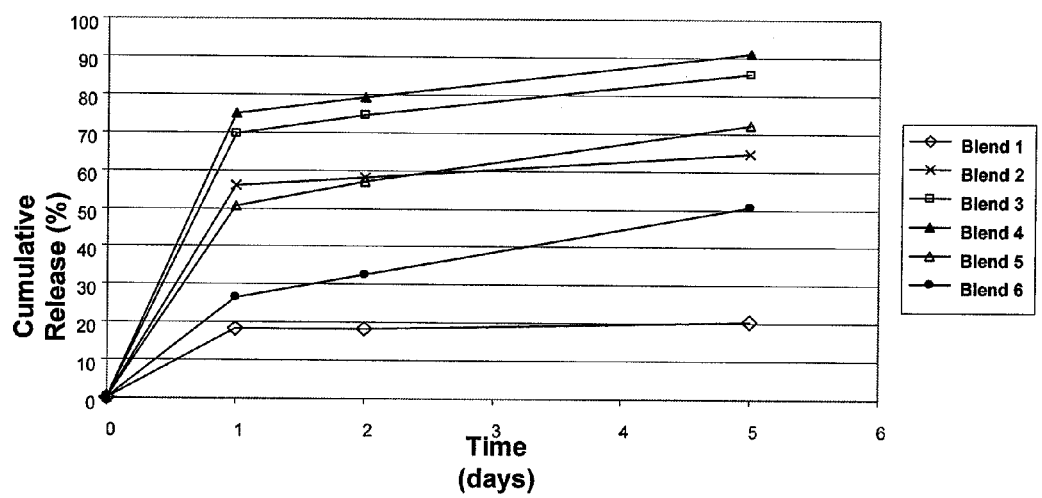
FIG. 3 is a graph of cumulative release of clonidine loaded PTMC pharmaceutical depots.

As illustrated in FIG. 2 and FIG. 3, the release profile of the post-operative pain relieving therapeutic agent utilizing the particular material or blend varies relative to the particular material or blend of poly(trimethylene carbonate). The cumulative release for some of the example is above 100%, this is attributed to the way the cumulative release values were generated. The cumulative release values were generated as calculated release values, not actual release values.

The pain relieving therapeutic agent can be any useful therapeutic agent that reduces or mitigates pain, when administered to a subject. In many embodiments the pain relieving therapeutic agent is a post-operative pain relieving therapeutic agent. The post-operative pain relieving therapeutic agent can be any useful agent that relieves or is indicated for relieving post-operative pain. Illustrative post-operative pain relieving therapeutic agents include, for example, local anesthetics and alpha or beta adrenergic agonists.

Local anesthetics includes, for example, benzocaine chloroprocaine, cocaine, cyclomethycaine, dimethocaine/larocaine, propoxycaine, procaine/novocaine, proparacaine, tetracaine/amethocaine, articaine, bupivacaine, carticaine, cinchocaine/dibucaine, etidocaine, levobupivacaine, lidocaine/lignocaine, mepivacaine, piperocaine, prilocalne, ropivacaine, and trimecaine. In many embodiments the local anesthetic is bupivacaine. The local anesthetic can be present in the flowable pharmaceutical depot in any therapeutic amount such as, for example, from 5 to 45%, or from 10 to 40% by weight.

Alpha or beta adrenergic agonists include for example, dobutamine, isoproterenol, salbutamol, fenoterol, formoterol, isoproterenolm, metaproterenol, salmeterol, terbutaline, clenbuterol, methoxamine, methylnorepinephrine, oxymetazoline, phenylephrine, clonidine, guanfacine, guanabenz, guanoxabenz, guanethidine, xylazine, and methyldopa. In many embodiments the alpha or beta adrenergic agonist is clonidine. The alpha or beta adrenergic agonist can be present in the flowable pharmaceutical depot in any therapeutic amount such as, for example, from 1 to 25%, or from 5 to 20% by weight.

EXAMPLES

Unless otherwise noted, all starting materials are commercially available from the Aldrich Chemical Company, Incorporated, Milwaukee Wis. (Aldrich).

Example 1

Depolymerization of Polylactic Acid with Dodecanol (Compound I)

Into a 100 mL round bottom flask, polylactic acid (i.e., polylactide available under the trade designation PURASORB® PLD 9665 from Purac Biomaterials, Purac America, Lincolmshire, Ill.) (inherent viscosity=5.71, 15.0 grams), 4-dimethylaminopyridine (DMAP, 9.16 grams), and dodecanol (5.59 grams) were charged and capped with rubber septum and placed in an oil bath at 140 degrees centigrade. The materials were heated at that temperature for 30 minutes after everything was melted and stirred freely with a magnetic stir bar. After cooling, 15 mL of tetrahydrofuran was added into the flask to dissolve the materials, and precipitated by adding heptane. After decanting off the solvents, the material was dissolved in chloroform (30 mL) and washed once with hydrochloride (1 molar, 20 mL, three times) and brine once. The solution was dried over anhydrous sodium sulfate. Yellow oil was obtained after solvent removal by rota-evaporation. (experimental Mn was about 800 g/mol by 1H-NMR end group analysis). Physical property results are show in Table 2 below.

Compounds II-VII were formed in a similar manner to Compound I as described above where the alcohol was replaced as described in Table 1 below. Compound VII utilized chloroform as the solvent

TABLE 1

| Compound ID | Alcohol | PLA/Alcohol Ratio | PLA/DMAP Ratio |
|---|---|---|---|
| I | Dodecanol | 2.68 | 1.64 |
| II | Butanol | 6.76 | 1.64 |
| III | Neopentanol | 5.68 | 1.64 |
| IV | 2-ethyl-1-butanol admantane | 4.90 | 1.64 |
| V | Methanol | 3.01 | 1.64 |
| VI | 1,3-butane diol | 5.56 | 1.64 |
| VII | 1,3-butane diol | 5.56 | 1.64 |

TABLE 2

| Compound ID | Reaction Temp (centigrade)/time (min) | Mn (g/mol) expt) | $T_g$ (centigrade) | Viscosity (Ps · sec at 25 deg centigrade) |
|---|---|---|---|---|
| I | 130/30 | 810 | −28 | 12 |
| II | 130/30 | 720 | −18 | 64 |
| III | 130/40 | 570 | −13 | 170 |
| IV | 130/30 | 830 | −50 | 0.94 |
| V | 130/30 | 420 | −16 | 70 |
| VI | 135/30 | 430 | −26 | 7 |
| VII | 35/2 days | 570 | −31 | Nd |

Example 2

Preparation of Drug Loaded PLA Formulation

Bupivacaine base was purchased from Orgamol (Switzerland). A IL prep of 10 mM phosphate buffer with 0.5 wt % sodium dodecyl sulfate (SDS) was made by addition of 0.372 g sodium phosphate monobasic (Aldrich), 1.96 g sodium phosphate dibasic (Aldrich), 5.0 g SDS (Aldrich), and deionized water. The pH of the 1 L buffer was adjusted to 7.4 by adding a few drops of 1M hydrochloric acid (Aldrich).

The drug loaded PLA formulations contained 70% (w/w) PLA compounds (Compounds I-VII) and 30% (w/w) bupivacaine base. The two components were added to a 2 cc transfer cup and mixed in a Flacktek, Inc. Speedmixer DAC 150 FVZ for 2 minutes. The mixed formulation was then back loaded into a 1 mL BD syringe with an 18G1.5 inch blunt tip needle.

Elution Testing:

100 uL of each drug loaded PLA formulation was injected in a 20 mL scintillation vial for drug elution testing. Each formulation was tested in triplicate and incubated in 10 mL of phosphate buffer with 0.5% (w/w) SDS pH 7.4 at 37° C. under mild agitation. At pre-selected times, the buffer was removed for analysis and replaced with fresh buffer medium. The drug content was quantified at 262 nm by Molecular Devices SpectraMax M2 (Sunnyvale, Calif.) plate reader.

The results of the elution testing are illustrated in FIG. 1.

Example 3

Synthesis of Trimethylene Carbonate Oligomers (i.e., Polytrimethylene Carbonates or PTMC)

The following illustrates the preparation of representative poly trimethylene carbonates. docecanol and the solvents are commercially available from Aldrich. Trimethylene carbonate monomer was purchased from Boehringer Ingelheim Chemicals, Petersburg, Va. All materials were used without further purifications. The reaction conditions, as well as the properties of resulting materials, are listed in the Table 3 and Table 4.

Into a 100 mL round bottom flask, trimethylene carbonate (25.0 g) and dodecanol (7.43 g) were charged and heated to melt in a 140 degrees centigrade oil bath under nitrogen. After the mixture was stirred at that temperature for 24 hours, the flask was allowed to cool to ambient temperature. Tetrahydrofuran (15 mL) was added to fully dissolve the material, followed by addition of heptane (40 mL) to make a two-phase separation. After settlement, the top solvent was decanted off and the residual solvent from the resulting oily material was removed under rotary evaporation. The product was further dried under full vacuum at 60 degrees centigrade till the weight remained constant. The average number of molecular weight (Mn) was determined by both 1H-NMR and gel permeation chromatography.

TABLE 3

| Compound ID | Alcohol | TMC/Alcohol Ratio | Reaction Temp (centigrade)/time (hours) |
|---|---|---|---|
| A | Dodecanol | 3.36 | 140/24 |
| B | Dodecanol | 7.10 | 140/78 |
| C | Dodecanol | 7.65 | 140/72 |
| D | Dodecanol | 2.78 | 140/72 |

TABLE 4

| Compound ID | Mn (g/mol) expt) | Mn (g/mol) GPC | Viscosity (Ps · sec at 25 deg centigrade) |
|---|---|---|---|
| A | 775 | 960 | |
| B | 1520 | 1520 | |
| C | 1390 | 1390 | 38 |
| D | 700 | 720 | 2.3 |

Example 4

Making Blends of Trimethylene Carbonate Oligomers

This is an example to demonstrate that the viscosity of a material can be tuned by mixing two trimethylene carbonate oligomers materials with different viscosities.

Six blends (Blend 1 through Blend 6 in Table 5 below) were achieved by mixing Material C and Material D from Table 4, in ratios indicated in Table 5. The mixture was mixed in a speed-mixer for 1 minute at 2500 rpms. The viscosity of each blend was measured using an Ares Rheometer.

TABLE 5

|  | Compound C % | Compound D % | Viscosity (Ps · sec at 25 deg centigrade) |
| --- | --- | --- | --- |
| Blend 1 | 0 | 100 | 2.3 |
| Blend 2 | 20 | 80 | 3.5 |
| Blend 3 | 40 | 60 | 6.5 |
| Blend 4 | 60 | 40 | 11 |
| Blend 5 | 80 | 20 | 22 |
| Blend 6 | 100 | 0 | 38 |

Example 5

Preparation of Drug Loaded Trimethylene Carbonate Oligomer Formulations

Clonidine HCl is commercially available from Spectrum Chemicals (Gardena, Calif.) and methanol is commercially available from Aldrich. Phosphate buffered saline is commercially available from Hyclone (Logan, Utah) and its pH was adjusted with 1M sodium hydroxide (Aldrich) to 7.4.

Clondine HCl was dissolved in methanol to yield a 12% (w/w) solution. The solution was spray dried in a Buchi B-290 Mini Spray Dryer (Buchi Laboratorium AG, Switzerland) using a 120 kHz Sono-Tek ultrasonic nozzle (Sono-Tek Corp., Milton, N.Y.). The processing parameters were set as follows: inlet temp. (70° C.), aspirator (80%), nitrogen inlet (50 mm), spray flow rate (80 mL/hr) and ultrasonic generator (0.8 watts). The spray dried powder was collected and dried for an additional 24 hours at 70° C. and 15 mmHg vacuum.

The drug loaded trimethylene carbonate oligomer formulations contained 98% (w/w) trimethylene carbonate oligomer compound (from above) and 2% (w/w) spray dried clonidine HCl. The two components were added to a 2 cc transfer cup and mixed in a Flacktek, Inc. Speedmixer DAC 150 FVZ for 2 minutes. The mixed formulation was then back loaded into a 1 mL BD syringe with an 18G1.5 inch blunt tip needle.

The drug loaded trimethylene carbonate oligomer formulations utilizing materials A, B and Blends 1, 2, 3, 4, 5, and 6 were tested as follows.
Elution Testing:

100 uL of the drug loaded trimethylene carbonate oligomer formulation was injected in a 20 mL scintillation vial for drug elution testing. The formulation was tested in triplicate and incubated in 10 mL of phosphate buffer saline pH 7.4 at 37° C. under mild agitation. At pre-selected times, the buffer was removed for analysis and replaced with fresh buffer medium. The drug content was quantified at 226 nm by Molecular Devices SpectraMax M2 (Sunnyvale, Calif.) plate reader.

The results of the elution testing are illustrated in FIG. 2 and FIG. 3.

Thus, embodiments of the FLOWABLE PHARMACEUTICAL DEPOT are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A method comprising:
   depolymerizing a polyester polymer with a primary alcohol to form an endcapped polyester polymer, wherein the primary alcohol comprises dodecanol and the polyester polymer comprises polylactic acid and the polylactic acid to dodecanol ratio is 2.68;
   adding 4-dimethylaminopyridine to the polylactic acid and the dodecanol, where the polylactic acid polymer to 4-dimethylaminopyridine ratio is 1.64; and
   combining the endcapped polyester polymer with a pain relieving therapeutic agent, forming a flowable pharmaceutical depot, wherein the pain relieving therapeutic agent comprises clonidine from 11 to about 20% by weight and where the flowable pharmaceutical depot does not cure or cross-link once administered in vivo.

2. A method according to claim 1, wherein the flowable pharmaceutical depot has a viscosity in a range from 0.1 to 500 Pa·s.

3. A method according to claim 1, wherein the pain relieving therapeutic agent further comprises bupivacaine.

4. A method according to claim 1, further comprising blending a first polyester polymer endcapped with a primary alcohol having a first molecular weight in a range from 500 to 3000 g/mol with a second polyester polymer endcapped with a primary alcohol having a second molecular weight in a range from 500 to 3000 g/mol, wherein the first molecular weight is different than the second molecular weight.

* * * * *